United States Patent
Prabhakarpandian et al.

(10) Patent No.: US 10,570,360 B2
(45) Date of Patent: Feb. 25, 2020

(54) MULTI-CHAMBERED CELL CULTURE DEVICE TO MODEL ORGAN MICROPHYSIOLOGY

(71) Applicant: CFD Research Corporation, Huntsville, AL (US)

(72) Inventors: Balabhaskar Prabhakarpandian, Madison, AL (US); Kapil Pant, Huntsville, AL (US)

(73) Assignee: CFD RESEARCH CORPORATION, Huntsville, AL (US)

(*) Notice: Subject to any disclaimer, the term of this patent is extended or adjusted under 35 U.S.C. 154(b) by 171 days.

(21) Appl. No.: 15/898,032

(22) Filed: Feb. 15, 2018

(65) Prior Publication Data
US 2018/0171277 A1 Jun. 21, 2018

Related U.S. Application Data

(62) Division of application No. 14/646,715, filed as application No. PCT/US2013/072081 on Nov. 26, 2013, now Pat. No. 9,932,550.

(60) Provisional application No. 61/730,357, filed on Nov. 27, 2012.

(51) Int. Cl.
*C12M 3/00* (2006.01)
*C12M 1/00* (2006.01)
(Continued)

(52) U.S. Cl.
CPC ............ *C12M 21/08* (2013.01); *C12M 23/20* (2013.01); *C12M 23/26* (2013.01); *C12M 23/58* (2013.01);
(Continued)

(58) Field of Classification Search
CPC ...... C12M 23/24; C12M 23/34; C12M 23/20; C12M 23/26; C12M 23/58; C12M 25/02;
(Continued)

(56) References Cited

U.S. PATENT DOCUMENTS 5,981,211 A 11/1999 Hu et al.
7,725,267 B2 5/2010 Prabhakarpandian et al.
(Continued)

FOREIGN PATENT DOCUMENTS

| WO | 0363262 A1 | 4/1990 |
| WO | 01-92462 A1 | 12/2001 |
| WO | 2012-022351 A1 | 2/2012 |

OTHER PUBLICATIONS

International Preliminary Report on Patentability in International Application No. PCT/US2013/072081.
(Continued)

*Primary Examiner* — Michael L Hobbs
(74) *Attorney, Agent, or Firm* — Maschoff Brennan; Jonathan M. Benns

(57) ABSTRACT

A method of testing an analyte can include using a cell culture device that includes: at least three distinct chambers between the top wall and bottom wall. The chambers can include: an internal chamber defined by at least one porous internal wall; one or more boundary layer chambers having at least an inner boundary layer chamber defined by the at least one porous internal wall and at least one porous inner boundary layer wall, the at least one porous internal wall having a plurality of pores fluidically coupling the central internal chamber to the one or more boundary layer chamber; and an outer chamber.

21 Claims, 10 Drawing Sheets

(51) Int. Cl.
   *C12M 1/12*   (2006.01)
   *C12M 1/36*   (2006.01)
(52) U.S. Cl.
   CPC ............ *C12M 25/06* (2013.01); *C12M 29/00* (2013.01); *C12M 29/04* (2013.01); *C12M 41/48* (2013.01)
(58) Field of Classification Search
   CPC ...... C12M 25/06; C12M 29/00; C12M 29/10; C12M 21/08; C12M 41/48
   See application file for complete search history.

(56)  References Cited

U.S. PATENT DOCUMENTS

| | | |
|---|---|---|
| 8,175,814 B2 | 5/2012 | Prabhakarpandian et al. |
| 8,589,083 B2 | 11/2013 | Prabhakarpandian et al. |
| 2006/0154361 A1* | 7/2006 | Wikswo ............ B01L 3/502746 435/289.1 |
| 2009/0023608 A1 | 1/2009 | Hung et al. |
| 2009/0203126 A1 | 8/2009 | Hung et al. |
| 2010/0099136 A1 | 4/2010 | Prabhakarpandian et al. |
| 2010/0112550 A1 | 5/2010 | Sundaram |
| 2010/0227312 A1 | 9/2010 | Pant et al. |
| 2011/0104658 A1 | 5/2011 | Prabhakarpandian et al. |
| 2011/0183312 A1 | 7/2011 | Huang et al. |

OTHER PUBLICATIONS

Prabhakarpandian, Balabhaskar, et al, SyM-BBB: a microfluidic Blood Brain Barrier model, Lab Chip 21 Mar. 2013, vol. 13, No. 6. pp. 1093-1101 See Figure 1: p. 1094.
International Search Report and Written Opinion in International Application No. PCT/US2013/072081.

* cited by examiner

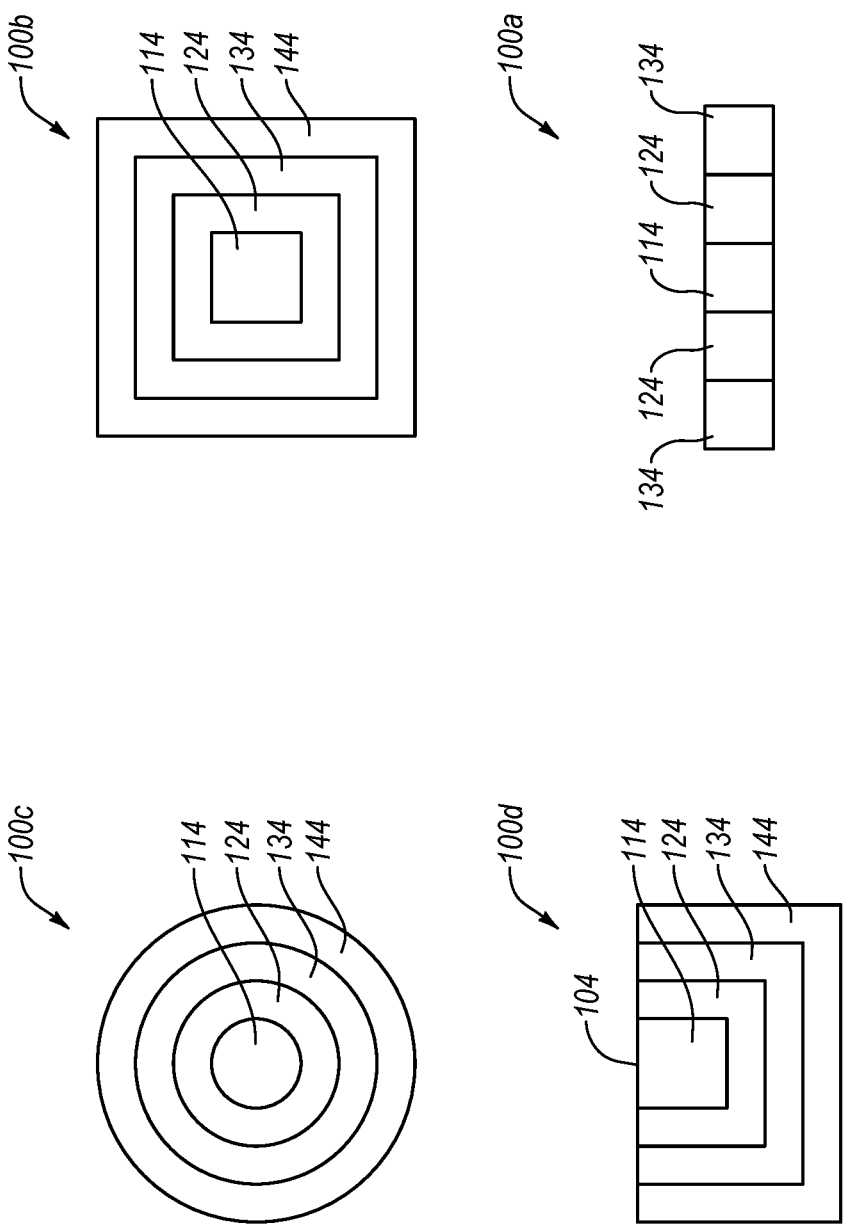

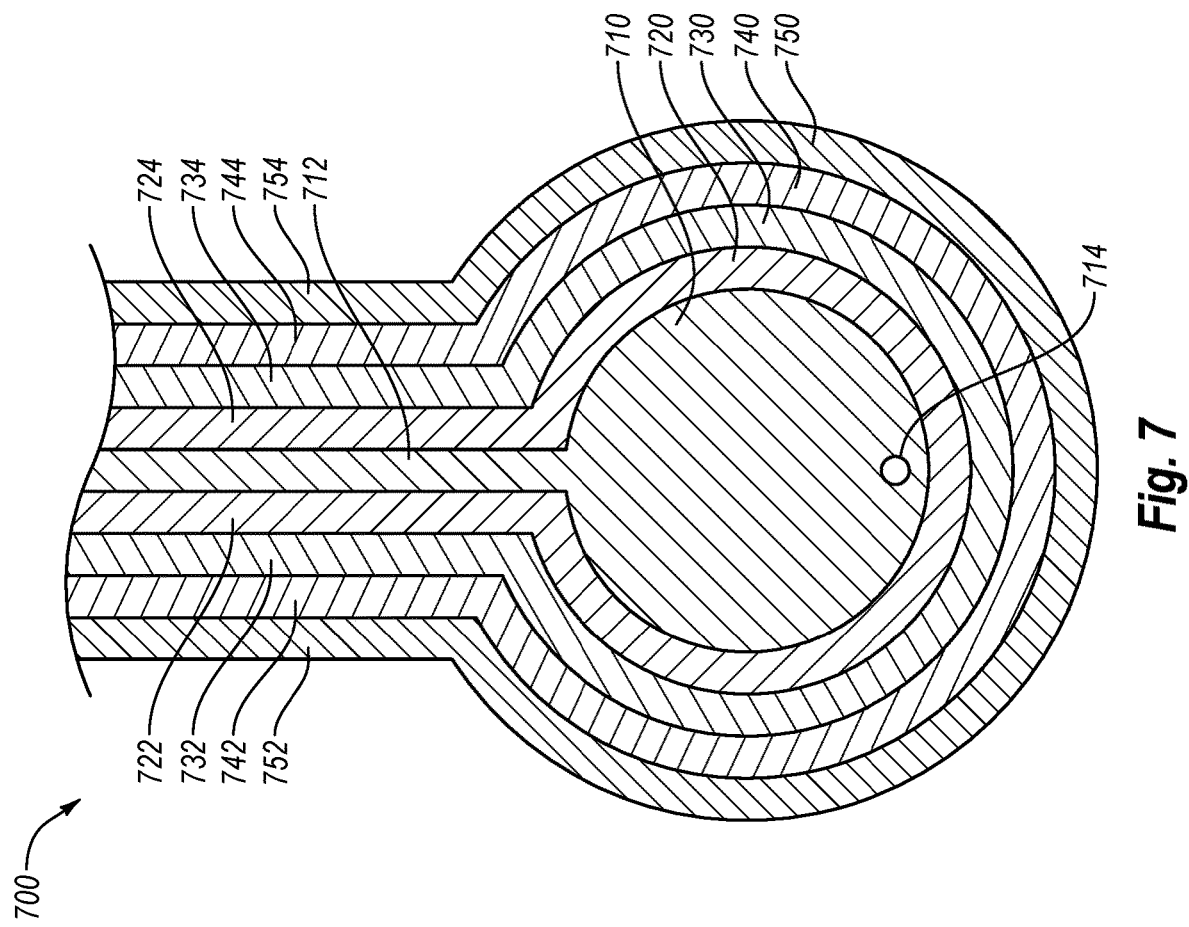

MULTI-CHAMBERED CELL CULTURE DEVICE TO MODEL ORGAN MICROPHYSIOLOGY

CROSS-REFERENCE

This patent application is a divisional of U.S. patent application Ser. No. 14/646,715 filed May 21, 2015, issued as U.S. Pat. No. 9,932,550 on Apr. 3, 2018, which is a nationalization of PCT Application No. PCT/US13/72081 filed Nov. 26, 2013, which claims priority to U.S. Provisional Patent Application 61/730,357 filed Nov. 27, 2012, which applications are incorporated herein by specific reference in its entirety.

BACKGROUND

Current in vitro platforms are poor predictors of in vivo safety, efficacy and pharmacokinetics of therapeutic agents or therapeutic delivery systems having therapeutic agents owing to significant difference in the test conditions compared to physiological conditions. Traditional in vitro models routinely utilize 2D monolayers of cultured cells under static conditions for studying drug delivery and toxicity. These simplistic representations often result in waste metabolite buildup in the platform, which can provide misleading information on the physiological condition. In order to overcome this limitation, perfused cell culture systems or bioreactors were developed to continuously replenish the culture medium. However, the use of continuously fed system leads to cost prohibitive reagent volume requirements. Microfluidic bioreactors were developed to address this challenge, and offer several key advantages over conventional macro-physiological systems (e.g., hollow fiber or membrane-based technologies). For instance, microfluidic systems offer facile compatibility with co-culture conditions, in particular multi-cellular architectures, real-time optical monitoring, and a more accurate representation of cell-cell interactions. However, available biomicroreactors fail to capture key in vivo physiological features such as morphological size, physiological blood flow and cellular (biological) architecture of the specific organs being investigated. Therefore, there remains a need for improved cell culture devices in order to enable improved modeling of organ and/or physiological response to therapeutic agents or therapeutic delivery systems having therapeutic agents.

BRIEF DESCRIPTION OF THE DRAWINGS

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 1B illustrates lateral cross-sectional views of embodiments of multi-chamber cell culture devices having idealized configurations.

FIG. 7 illustrates an embodiment of a multi-chamber cell culture device with a central chamber with a planar inlet and non-planar outlet with lateral chambers having circumferential pathways with inlets and outlets on a common side in an idealized configuration.

Figure 1A:
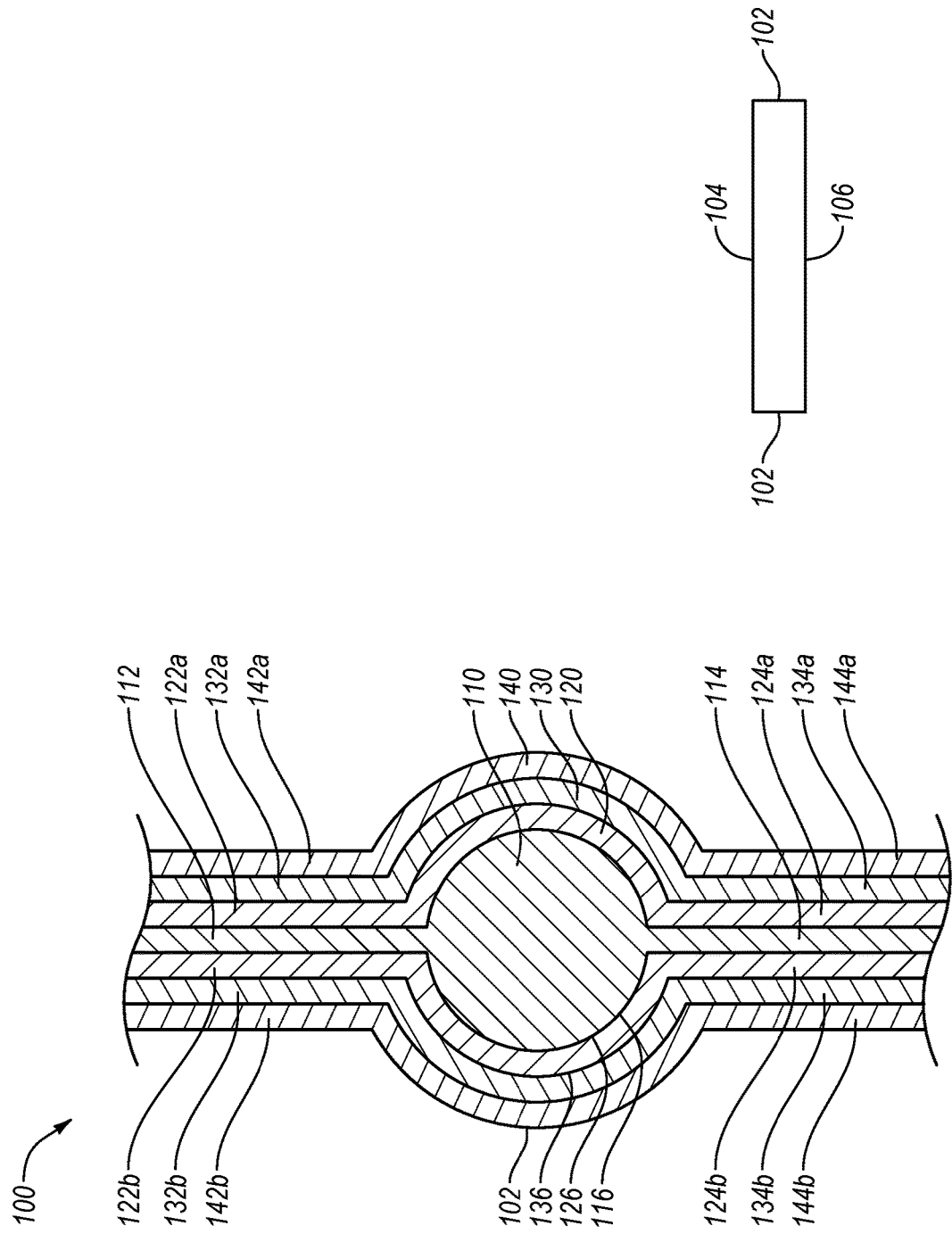
FIG. 1A illustrates an embodiment of a multi-chamber cell culture device in an idealized configuration.

All aspects of the embodiments described in the figures can be used in conjunction with other embodiments in other figures. For example, posts can be used in a barrier layer or barrier conduit without being used in the central or interior chamber. Also, the figures are not to scale or dimension. For example, the distances between chambers may be different with respect to other distances between other chambers. While some aspects are shown to be symmetrical, those aspects may be asymmetrical.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention relates to a multi-chamber cell culture device that can provide improved organ models as well as methods of making and using the same. The multi-chamber cell culture device can include an outer chamber that can be used as an outer conduit and an internal chamber that can be used as an internal organ tissue space separated by one or more barrier chambers (e.g., barrier layer chambers). As such, the multi-chamber cell culture device can be a construct with an outer chamber and a central chamber separated by one or more barrier chambers there between. The multi-chamber cell culture device can include one or more of the outer chamber, one or more barrier chambers, and central being a cell culture chamber. The multi-chamber cell culture device can include one or more of the outer chamber, one or more barrier chambers, and central being devoid of cell cultures. The multi-chamber cell culture device can include an outer conduit (e.g., outer chamber) and an internal organ tissue space (e.g., central chamber) separated by one or more barrier layers (e.g., barrier chambers). In one aspect, an internal organ tissue space (e.g., central chamber) may be offset or off-center or asymmetrical with respect to the outer chamber and barrier chambers, and thereby may be referenced as an internal chamber that is surrounded by the barrier chambers that are surrounded by the outer chamber. This provides the chambers in an onion layer arrangement.

The conduit, organ tissue space, and one or more organ barrier layers can be distinct chambers that are partitioned from each other with porous walls. The porous walls can have true pores or have gaps between wall sections or gaps between barrier pillars or posts that function as pores so that fluid and nutrients and test analytes can pass between the distinct chambers. In one option, the pores can be gaps that are large enough for cancer cells to pass therethrough, such as for cancer metastasis modeling or for cell migration. The porous walls can be configured to keep the chambers distinct from each other while the pores in the porous walls can allow for nutrients to move therebetween. This configuration can provide for modeling of an organ.

Generally, any of the chambers, such as the outer chamber, inner chamber, boundary layer chambers, inner organ tissue space chamber, one or more organ barrier layers, or other distinct region in the multi-chamber construct can be distinct chambers that are partitioned from each other with porous walls and used for tissue culture spaces. For example, the outer chamber and/or any barrier chamber and/or any combination thereof with or without the internal chamber can be used as a tissue culture chamber. Oppositely, the outer chamber and/or any barrier chamber and/or any combination thereof with or without the central chamber can be used without having any cell culture therein.

The incorporated references describe idealized microvascular networks (IMN) and synthetic microvascular networks (SMN), which can be included in the inlets, outlets or chambers therebetween. That is, an IMN can include one or more multi-chambered cell culture constructs in an IMN configuration; or a SMN can include one or more multi-chambered cell culture constructs in an SMN configuration; or a hybrid IMN/SMN can include fluid pathways that include features of IMN and/or SMN and one or more multi-chambered cell culture constructs with the IMN or SMN configuration. Accordingly, the multi-chamber cell culture device can be configured with distinct chambers that are modeled by IMN and/or SMN. Some configurations can include only IMN chambers, some may include only SMN chambers, and some can include a combination of both IMN and SMN chambers. The multi-chamber cell culture device can be configured for any organ with an appropriate outer conduit simulating an organ, one or more barrier layer conduits simulating a barrier membrane of an organ, and an organ tissue space configured as the tissue that provides the organ function. For example, the multi-chambered cell culture device can simulate the liver, kidney, heart, lung, brain, stomach, intestine, blood brain barrier, vascular networks, or others. As such, the distinct chambers can have unique cell cultures that are indicative of the different cell types or tissue types of the different layers and central region of an organ, where the cell culture in the outer conduit chamber can be different from the organ barrier layer chambers, which can be different from the internal organ tissue chamber. A single embodiment of the multi-chambered cell culture device can be configured to be different organs by the different cells or cell combinations that are present in the distinct cell cultures of the distinct chambers. That is, different types of cells and cell combinations can distinguish a device simulating the heart from a device simulating the liver, where without the cells the devices can appear similar or identical.

The multi-chambered cell culture device can include a fluid inlet and fluid outlet for each of the distinct chambers. The fluid inlets and outlets can be adjacent or distributed about the device, or random on the device. The fluid outlet of one device can be fluidly coupled to the inlet of another device so that multiple simulated organs can be linked (see FIG. 10). For example, a metabolic pathway or organ series can be mimicked by linking multiple devices through their inlets and outlets. For example, a series of simulated organ devices can be: lung; liver; heart; and kidney. The linked devices may be in series and/or in parallel (see FIG. 11), and may be linear or may include branches (see FIGS. 11 and 12). For example, a liver device may be fluidly coupled to a downstream brain device and a kidney device. As such, the fluid inlets and outlets can be bifurcated. Such bifurcations can be idealized (e.g., IMN) or synthetic (e.g., SMN). The multi-chambered cell culture device can include one or more IMN or SMN networks coupled to one or more of the inlets or outlets of one or more of the individual chambers of the multi-chambers.

The multi-chambered cell culture device can be configured to be retained in any common cell culture incubator or other common laboratory equipment used for growing, propagating, and analyzing cell cultures. The inlets and outlets can be configured to be coupled to tubing, cell culture pumps, syringe pumps, or other cell culture equipment or pumps that can move fluid through the fluid inlets and outlets as well as through the distinct chambers. Unique pumps can be coupled to the different chambers.

FIG. 1A shows an embodiment of a multi-chambered cell culture device 100 in accordance with the principles of the present invention. The multi-chambered cell culture device 100 is shown to include an internal chamber 110 (e.g., internal organ tissue chamber), an inner boundary layer chamber 120, an outer boundary layer chamber 130, and an outer conduit layer chamber 140. However, only one boundary layer chamber or more than two additional boundary layer chambers can be located between the internal chamber 110 and outer conduit layer chamber 140. That is, the multi-chambered cell culture device 100 can include one or more internal chambers 110 (or central chambers), one or more inner boundary layer chambers 120, one or more outer boundary layer chambers 130, and one or more outer conduit layer chamber 140. As such, any of the chambers can be partitioned into a plurality of chambers with porous walls. It should be noted that the internal chamber 110 is designated as a tissue chamber due to certain use embodiments; however, such internal chamber 110 may not be used as a tissue chamber or cell culture chamber, and may be used as an internal or central chamber. The internal chamber may also be used for 2D cell cultures or monolayers, which can be applied to any of the chambers. The internal chamber 110 can include a fluid inlet 112 and a fluid outlet 114. The inner boundary layer chamber 120 can include at least one fluid inlet 122*a* and 122*b*, which can be fluidly coupled or fluidly separate, and include at least one fluid outlet 124*a* and 124*b*, which can be fluidly coupled or fluidly separate. The outer boundary layer chamber 130 can include at least one fluid inlet 132*a* and 132*b*, which can be fluidly coupled or fluidly separate, and include at least one fluid outlet 134*a* and 134*b*, which can be fluidly coupled or fluidly separate. The outer conduit layer chamber 140 can include at least one fluid inlet 142*a* and 142*b*, which can be fluidly coupled or fluidly separate, and include at least one fluid outlet 144*a* and 144*b*, which can be fluidly coupled or fluidly separate. The internal chamber 110 can be defined by a porous tissue chamber wall 116, the inner boundary layer chamber 120 can be defined by the porous tissue chamber wall 116 and a porous boundary layer wall 126, the outer boundary layer chamber 130 can be defined by the porous boundary layer wall 126 and a porous outer conduit wall 136, and the outer conduit layer chamber 140 is defined by the porous outer conduit wall 136 and an external wall 102 that is not porous. As also shown, the external wall 102 can be a side wall between a top wall 104 and a bottom wall 106, which may be coupled or integrated. For example, the bottom wall 106 can be integrated with the external wall 102 and porous walls, and the top wall 104 can be coupled to the external wall and porous walls. The top wall 104 can be a lid. The right and left sides can cooperate to form the boundary layer chamber and outer conduit chamber, or they may be distinct right and left side chambers that are configured as boundary layer chambers or outer conduit chambers.

While not specifically shown, the inlets and outlets may each individually include inlet valves and outlet valves, which can be selectively opened to allow fluid flow or pressure and closed for incubation.

While the inlets 122*a* and 122*b* for the inner boundary layer chamber 120 are shown to be separate, they may be fluidically coupled. Also, the outlets 122*a* and 122*b* may also be separate or fluidically coupled. The other inlets and outlets for the discrete chambers may also be separate or fluidically coupled. Such fluid coupling can be by tubing or other fluid conduits coupled to both inlets or both outlets, or the device can be structured in three-dimensions with a fluid pathway passing over or under a different fluid pathway. Also, while the discrete chambers are shown to have left sides that are separate from right sides, the lateral chambers may indeed be separate or they may be fluidically coupled by passing the individual chambers over or under other chambers. A myriad of design choices are available under the teachings provided herein.

FIG. 1B shows a linear multi-chamber embodiment 100*a* where the inlets and/or chambers and/or outlets are separate and aligned in a plane. Also, a squared concentric multi-chamber embodiment 100*b* where the inlets and/or chambers and/or outlets are squared concentric, and is shown with the internal chamber outlet 114 being squared concentric with the other outlets 124, 134, and 144. Also, the inlets and/or chambers and/or outlets can be round concentric with round cross-sectional profiles as shown in round concentric multi-chamber embodiment 100*c*, or concentric with polygon cross-sectional profiles. Additionally, the inlets and/or chambers and/or outlets are can be semi-concentric as in semi-concentric multi-chamber embodiment 100*d* with a common top wall 104. Also, the outlet configurations of FIG. 1B can be applied to the inlets as well as to the body of the device that has the distinct conduits. That is, any of the inlets, outlets, or the distinct conduits could be arranged as illustrated in FIG. 1B, or any combination of the illustrations, e.g., round semi concentric.

Figure 4:
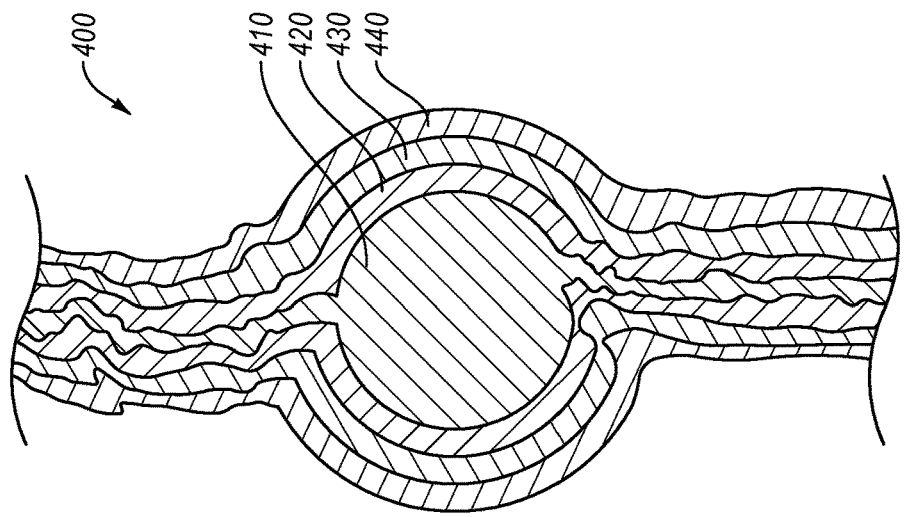
FIG. 4 illustrates an embodiment of a multi-chamber cell culture device having inlets and outlets having synthetic microvascular network (SMN) configurations and the multi-chambers having an idealized configuration.
Figure 3:
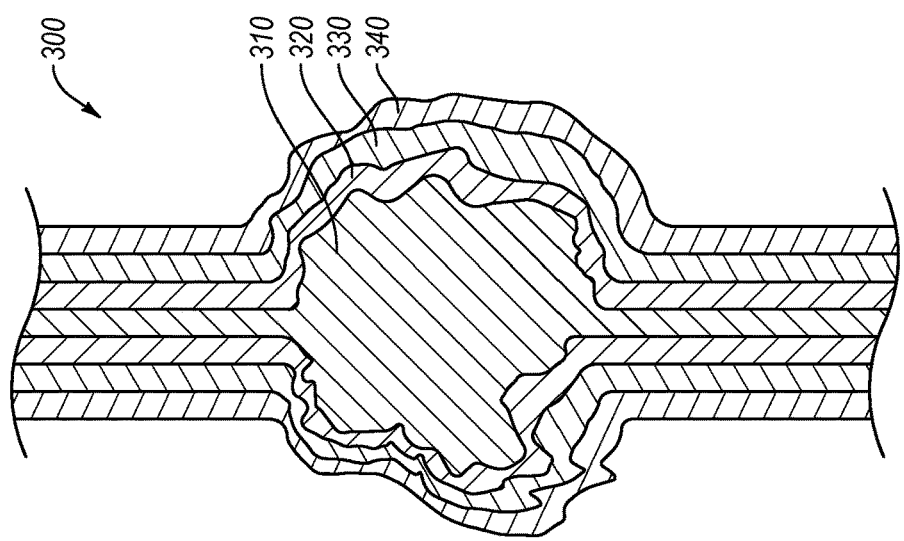
FIG. 3 illustrates an embodiment of a multi-chamber cell culture device having inlets and outlets having idealized configurations and the multi-chambers in a synthetic microvascular network (SMN) configuration.
Figure 2:
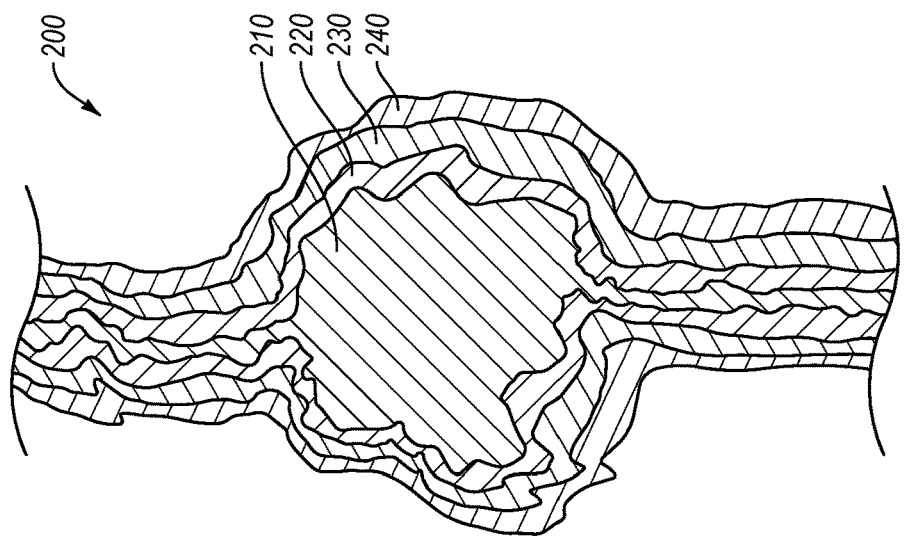
FIG. 2 illustrates an embodiment of a multi-chamber cell culture device in a synthetic microvascular network (SMN) configuration.

While FIG. 1A shows a generally idealized configuration that may include features of an IMN network, FIG. 2 shows the multi-chambered cell culture device 200 can include irregular or simulated inlets, chambers, and outlets, such as in an SMN. Here, the internal chamber 210, inner barrier layer chamber, 220, outer barrier layer chamber 230, and outer conduit layer 240 can all be irregular or modeled after an SMN network. FIG. 3 shows that device 300 can include IMN inlets and outlets with the internal chamber 310, inner barrier layer chamber, 320, outer barrier layer chamber 330, and outer conduit layer 340 being irregular or SMN-like. FIG. 4 shows the device 400 can include SMN inlets and outlets with the internal chamber 410, inner barrier layer chamber, 420, outer barrier layer chamber 430, and outer conduit layer 440 being idealized or IMN-like. However, the IMN and/or SMN configurations and shaping shown in FIGS. 1A and 2-4 can be combined or used with other devices as described herein. For example, some of the distinct chambers may be IMN and some may be SMN, which also may be applied to some of the inlets and outlets.

Figure 5:
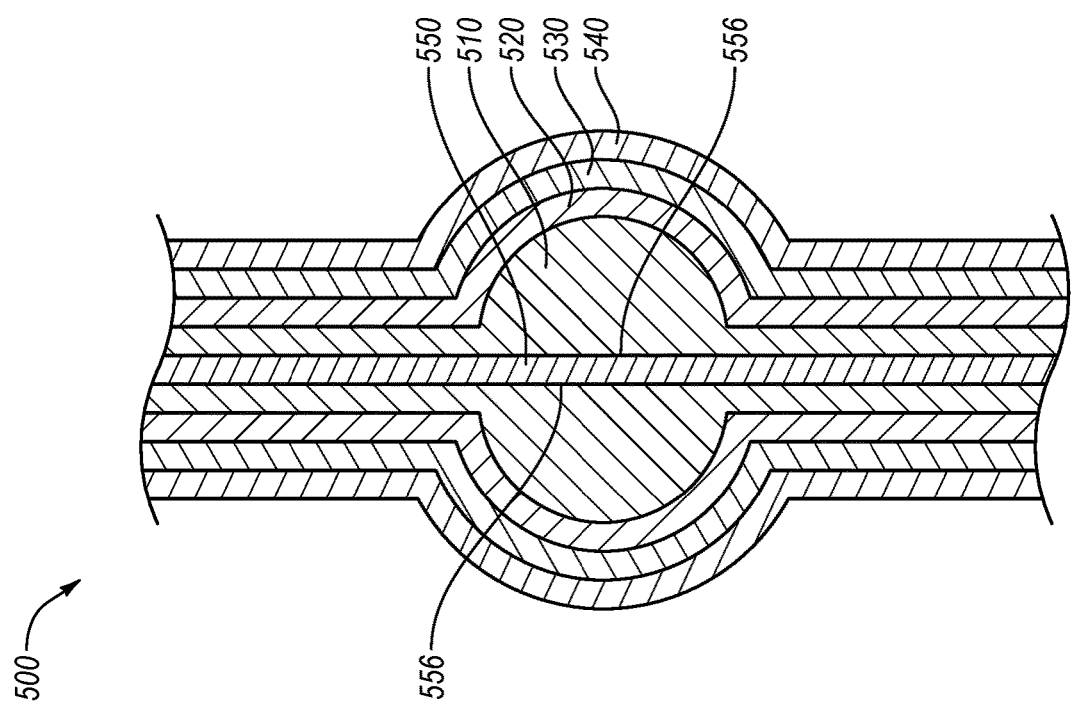
FIG. 5 illustrates an embodiment of a multi-chamber cell culture device with a pass-through passageway in an idealized configuration.

FIG. 5 shows a multi-chambered cell culture device 500 that has an internal conduit 550 that is within the internal chamber 510. The inner barrier layer chamber, 520, outer barrier layer chamber 530, and outer conduit layer 540 are configured as described herein. Here, the internal conduit 550 can be defined by a porous wall 556 such that fluid and/or nutrients can pass between the internal conduit 550 and the internal chamber 510.

Figure 6:
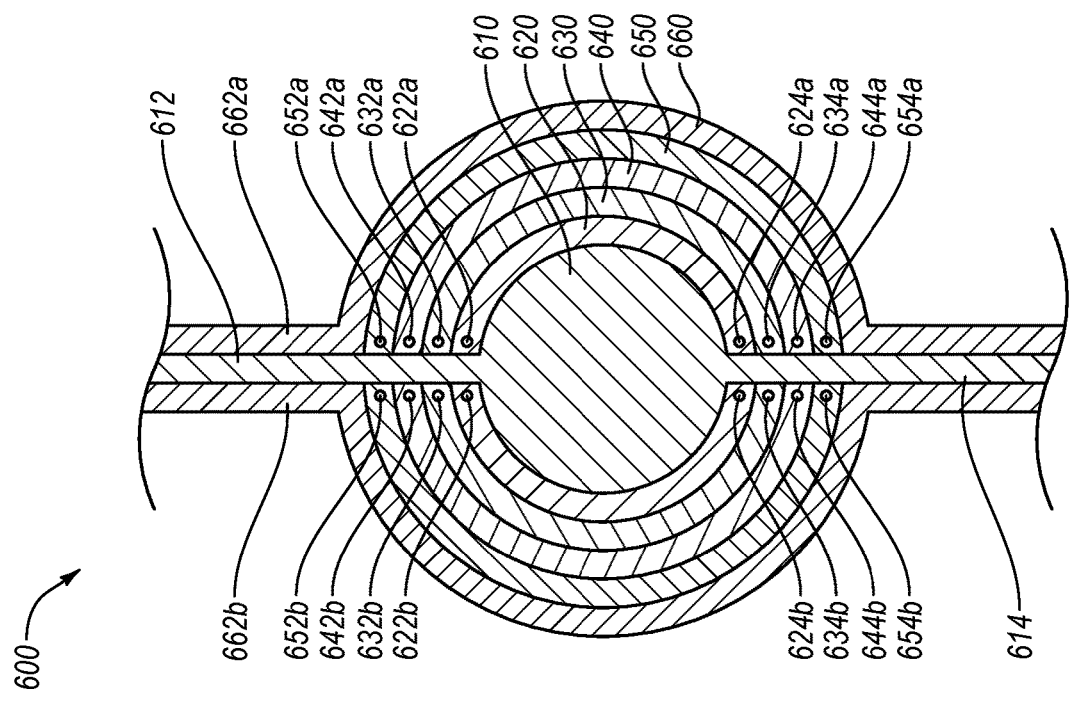
FIG. 6 illustrates an embodiment of a multi-chamber cell culture device with a non-planar inlets and outlets in an idealized configuration.

FIG. 6 shows another multi-chambered cell culture device 600 configured similar to other embodiments shown herein with the internal chamber 610 having an inlet 612 and outlet 614 that are configured similar to fluid pathways in the substrate (e.g., bottom wall). The outer chamber 660 also has one or more inlets 662*a* and 662*b* and one or more outlets 664*a* and 664*b* that are configured similar to fluid pathways in the substrate (e.g., bottom wall). However, the boundary layer chambers 620, 630, 640, and 650 have port inlets (e.g., 622*a* and 622*b*, 632*a* and 632*b*, 642*a* and 642*b*, and 652*a* and 652*b*) that may or may not include port valves, and port outlets (e.g., 624*a* and 624*b*, 634*a* and 634*b*, 644*a* and 644*b*, and 654*a* and 654*b*) that may or may not include port valves. Tubing or other fluid pathways may be coupled to the inlets and/or outlets, which may further be coupled to pumps, fluid reservoirs, media reservoirs, or other cell culture components. Also, any of the inlets can be fluidly coupled or fluidly separate upstream from the inlet, and any of the outlets can be fluidly coupled or fluidly separate downstream from the outlets as described herein.

FIG. 7 shows another embodiment of a multi-chambered cell culture device 700, which includes an internal chamber 710 having a fluid pathway inlet 712 and a port outlet 714, which may include a tubing with or without a valve. The barrier layer chambers (e.g., 720, 730, and 740) can wrap around the internal chamber 710 and include inlets (e.g., 722, 732, and 742) on one side of the fluid pathway inlet 712 and outlets (e.g., 724, 734, and 744) on the other side of the fluid pathway inlet 712. This can be a circumferential pathway configuration with inlets and outlets on a common side or end. The outer chamber 750 is also circumferentially positioned and includes similarly arranged inlet 752 and outlet 754. Here, the outer chamber 750 is in fluid communication with the barrier layer chamber 740 from the inlets to the outlets, and the barrier layer chamber 720 is in fluid communication with the internal chamber 710 from the inlets to the outlets. The internal walls are porous, which allows the analytes to pass between the distinct chambers from the inlet through to the outlet as well as the cells in one chamber to communicate with cells in the adjacent chamber.

The porous walls can be configured to provide a diffusion barrier between adjacent chambers. This can provide a diffusion barrier between the vascular space (e.g., outer conduit chamber) and tissue space (e.g., internal chamber).

Figure 8:
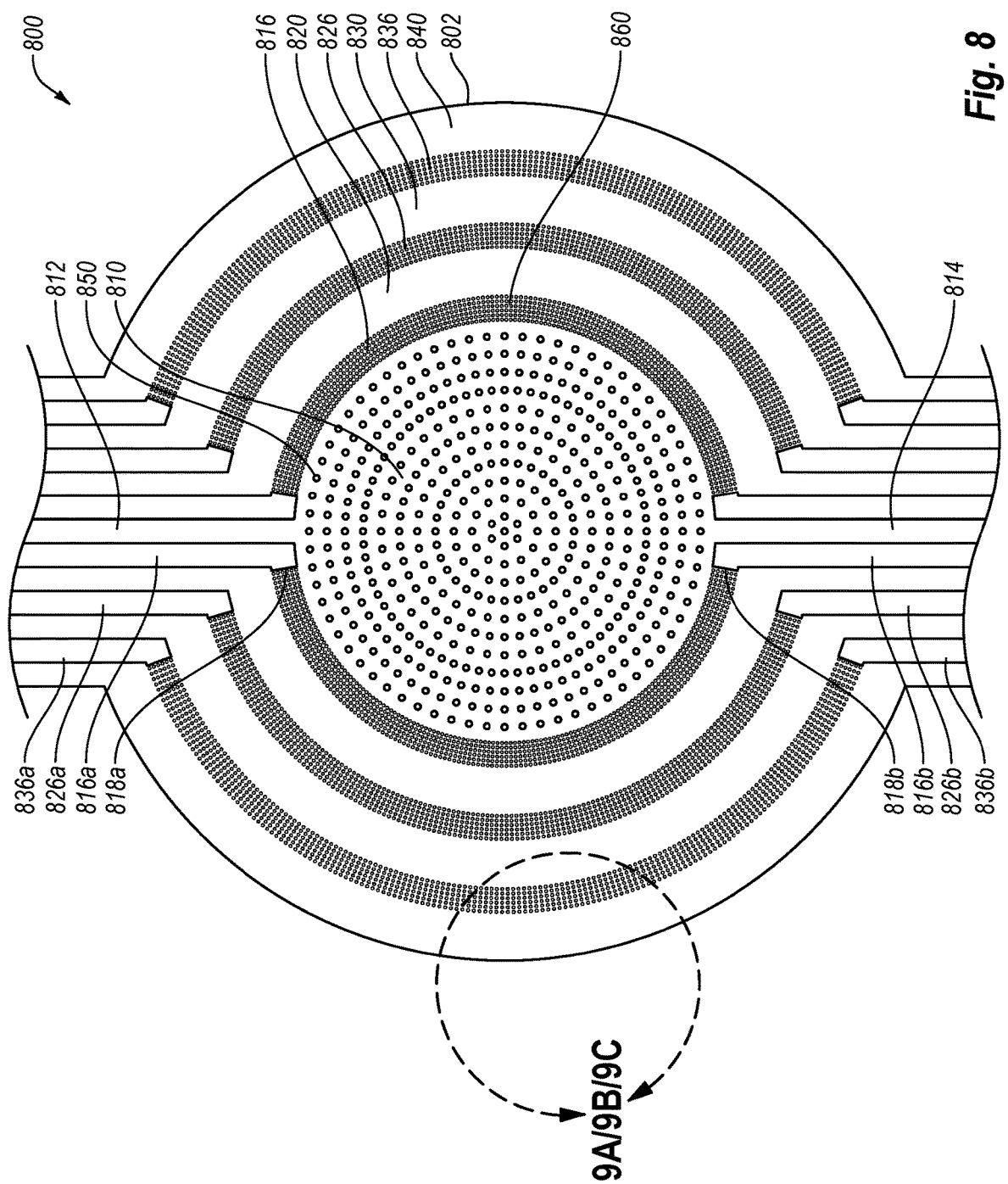
FIG. 8 illustrates an embodiment of a multi-chamber cell culture device with central chamber with internal pillars or posts and barrier pillars or posts forming porous walls between the chambers in an idealized configuration.
Figure 9A:
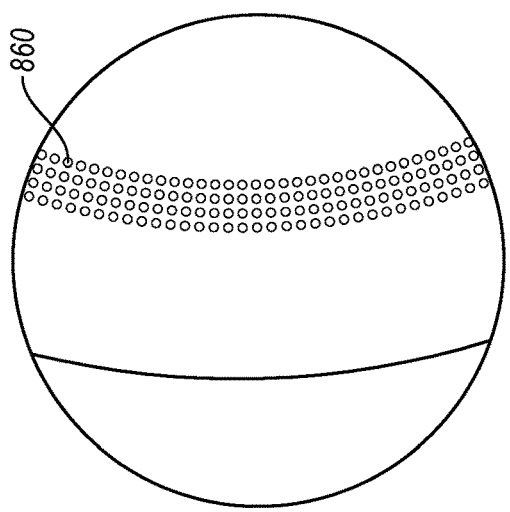
FIGS. 9A-9C illustrate different embodiments of barrier pillars or posts forming porous walls.
Figure 9B:
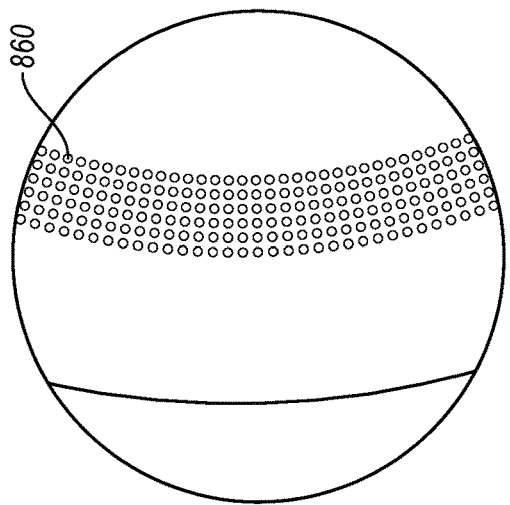
Figure 9C:
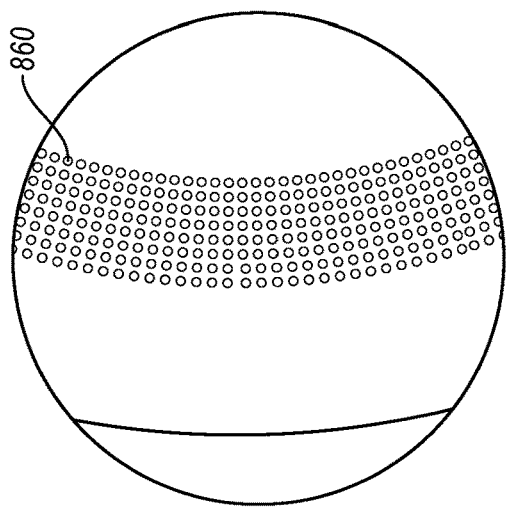

FIG. 8 shows another embodiment of a multi-chambered structure 800 in accordance with the principles of the present invention. The multi-chambered cell culture device 800 is shown to include an internal chamber 810, an inner boundary layer chamber 820, an outer boundary layer chamber 830, and an outer conduit layer 840. However, only one boundary layer chamber or more than two additional boundary layer chambers can be located between the internal chamber 810 and outer conduit layer 840. The internal chamber 810 can include a fluid inlet 812 and a fluid outlet 814. The inner boundary layer chamber 820 can include at least one fluid inlet and at least one fluid outlet as described herein. The outer boundary layer chamber 830 can include at least one fluid inlet and at least one fluid outlet as described herein. The outer conduit layer 840 can include at least one fluid inlet and at least one fluid outlet as described herein. The internal chamber 810 can be defined by a porous tissue chamber wall 816, the inner boundary layer chamber 820 can be defined by the porous tissue chamber wall 816 and a porous boundary layer wall 826, the outer boundary layer chamber 830 can be defined by the porous boundary layer wall 826 and a porous outer conduit wall 836, and the outer conduit layer 840 is defined by the porous outer conduit wall 836 and an external wall 802 that is not porous. Here, the porous walls 816, 826, 836 can include a plurality of posts 860 that form the walls with the gaps between the posts 860. The porous walls 816, 826, 836 have one or more posts 860 laterally or radially oriented to form the walls. FIGS. 9A-9C the porous walls can include any number of laterally or radially oriented posts 860 between chambers, where 4 posts, 6 posts, and 8 post embodiments are shown, but any number of posts 860 can be used as the porous walls, including a line of single posts 860 forming the porous walls 816, 826, 836.

In one embodiment, the porous walls 816, 826, 836 can be configured as conduits or chambers, and may include inlets 816a, 826a, 836a, and/or outlets 816b, 826b, 836b.

In one embodiment, the porous walls 816, 826, 836 are not conduits or chambers, and are configured as barrier walls. Here, the porous walls 816, 826, 836 may be devoid of inlets 816a, 826a, 836a, and/or outlets 816b, 826b, 836b. As shown for porous wall 816, an inlet barrier wall 818a and/or outlet barrier wall 818b can be included.

It should be recognized that the porous walls having the one or more lateral or radial posts, post array, post line, or any other orientation or distribution of posts 860 can be applied to any of the barrier walls between any of the chambers/conduits of any of the other embodiments or figures herein. The posts can have an even spacing therebetween or asymmetrical spacing. The posts can be uniform in size or have size distributions along a pathway or chamber or through the wall from one chamber to anther chamber.

In one embodiment, any of the chambers/conduits can include structure posts 850 that can be used to provide structure between top walls and bottom walls. The structure posts 850 can be coupled to a bottom wall, and may be coupled to a top wall when integrated with the side walls. Also, the top wall as a lid can rest on the structure posts 850. The structure posts can be used for cell culture, and can result in a higher cell density for organ simulations. FIG. 8 shows the central chamber 810 as having the posts 850, but it can be devoid of posts. Any of the boundary chambers 820, 830 can include the posts 850 or be devoid of posts. The outer chamber 840 can include the posts 850 or be devoid of posts.

Figure 10:
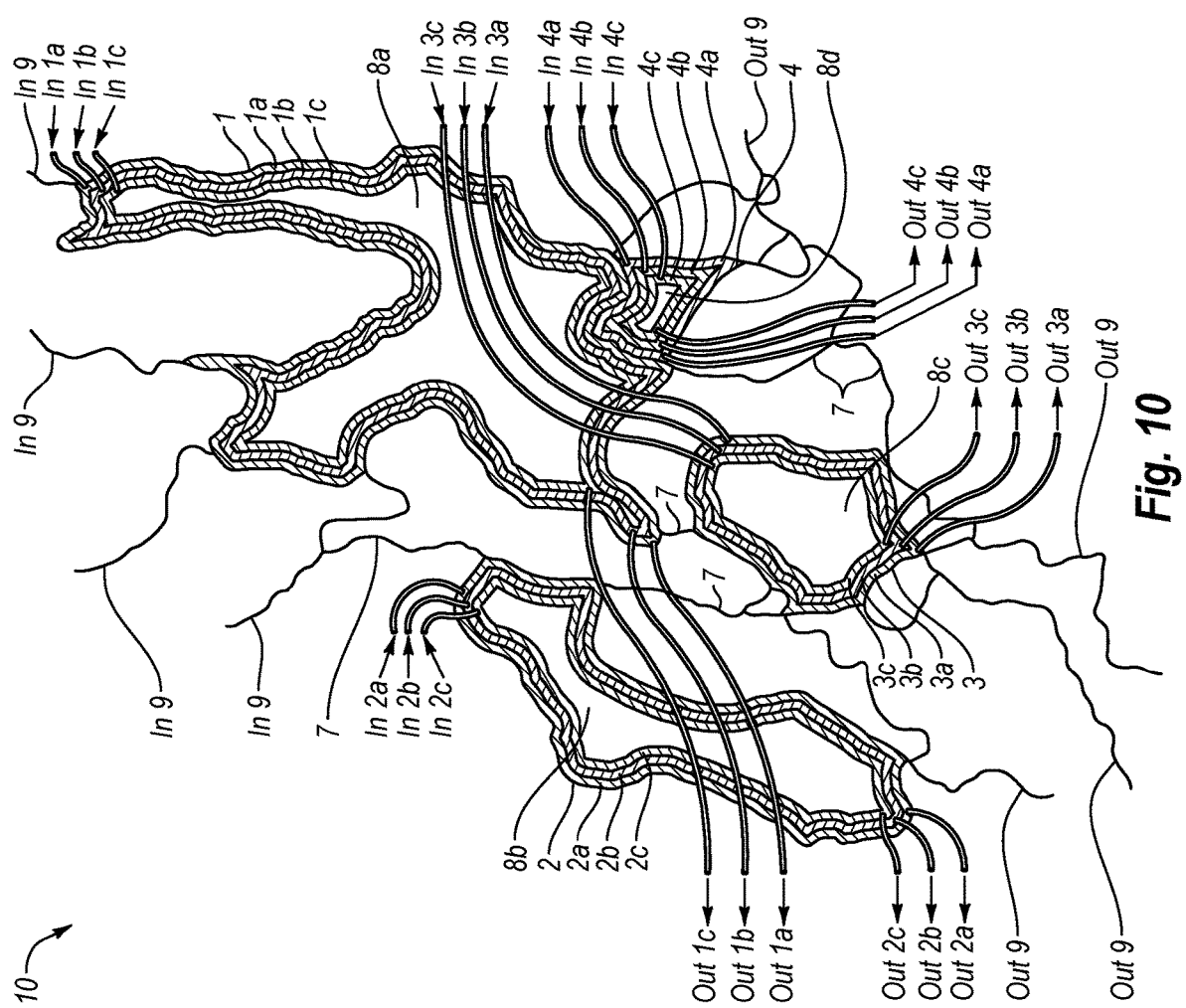
FIG. 10 illustrates an embodiment of SMN network having SMN fluid pathways and SMN multi-chambered cell culture constructs.

FIG. 10 illustrates a SMN 10 having one of more fluid inlets In 9 and one or more fluid outlets Out 9 with one or more multi-chamber constructs 1, 2, 3, 4, each having a central chamber 8a, 8b, 8c, 8d (e.g., while four multi-chamber constructs are shown, any integer can be used). The multi-chamber constructs 1, 2, 3, 4 can be configured with inlets and outlets in accordance with any of the embodiments or figures described herein. Also, while shown to be SMN, the configuration can be an IMN. The SMN can be configured with any number of fluid pathways 7 linking the multi-chamber constructs, which can be in any manner, and which SMN can be designed via simulation of real biological or artificial fluid pathways.

As shown, multi-chamber construct 1 can include a central chamber 8a surrounded by an outer conduit layer 1a with barrier layer chambers 1b, 1c therebetween. The outer conduit layer 1a can be fluidly coupled with an inlet In 9 and an outlet Out 9. Also, the outer conduit layer 1a can include an inlet In 1a and an outlet Out 1a. The barrier layer chambers 1b, 1c, can include inlets In 1b, In 1c and outlets Out 1b, Out 1c, respectively. While not shown, the central chamber 8a can include inlets or outlets, or it can receive content from the barrier layer 1c.

As shown, multi-chamber construct 2 can include a central chamber 8b surrounded by an outer conduit layer 2a with barrier layer chambers 2b, 2c therebetween. The outer conduit layer 2a can be fluidly coupled with an inlet In 9 and an outlet Out 9. Also, the outer conduit layer 2a can include an inlet In 2a and an outlet Out 2a. The barrier layer chambers 2b, 2c, can include inlets In 2b, In 2c and outlets Out 2b, Out 2c, respectively. While not shown, the central chamber 8b can include inlets or outlets, or it can receive content from the barrier layer 2c.

As shown, multi-chamber construct 3 can include a central chamber 8c surrounded by an outer conduit layer 3a with barrier layer chambers 3b, 3c therebetween. The outer conduit layer 3a can be fluidly coupled with an inlet In 9 and an outlet Out 9. Also, the outer conduit layer 3a can include an inlet In 3a and an outlet Out 3a. The barrier layer chambers 3b, 3c, can include inlets In 3b, In 3c and outlets Out 3b, Out 3c, respectively. While not shown, the central chamber 8a can include inlets or outlets, or it can receive content from the barrier layer 3c.

As shown, multi-chamber construct 4 can include a central chamber 8d surrounded by an outer conduit layer 4a with barrier layer chambers 4b, 4c therebetween. The outer conduit layer 4a can be fluidly coupled with an inlet In 9 and an outlet Out 9. Also, the outer conduit layer 4a can include an inlet In 4a and an outlet Out 4a. The barrier layer chambers 4b, 4c, can include inlets In 4b, In 4c and outlets Out 4b, Out 4c, respectively. While not shown, the central chamber 8d can include inlets or outlets, or it can receive content from the barrier layer 4c.

Figure 11:
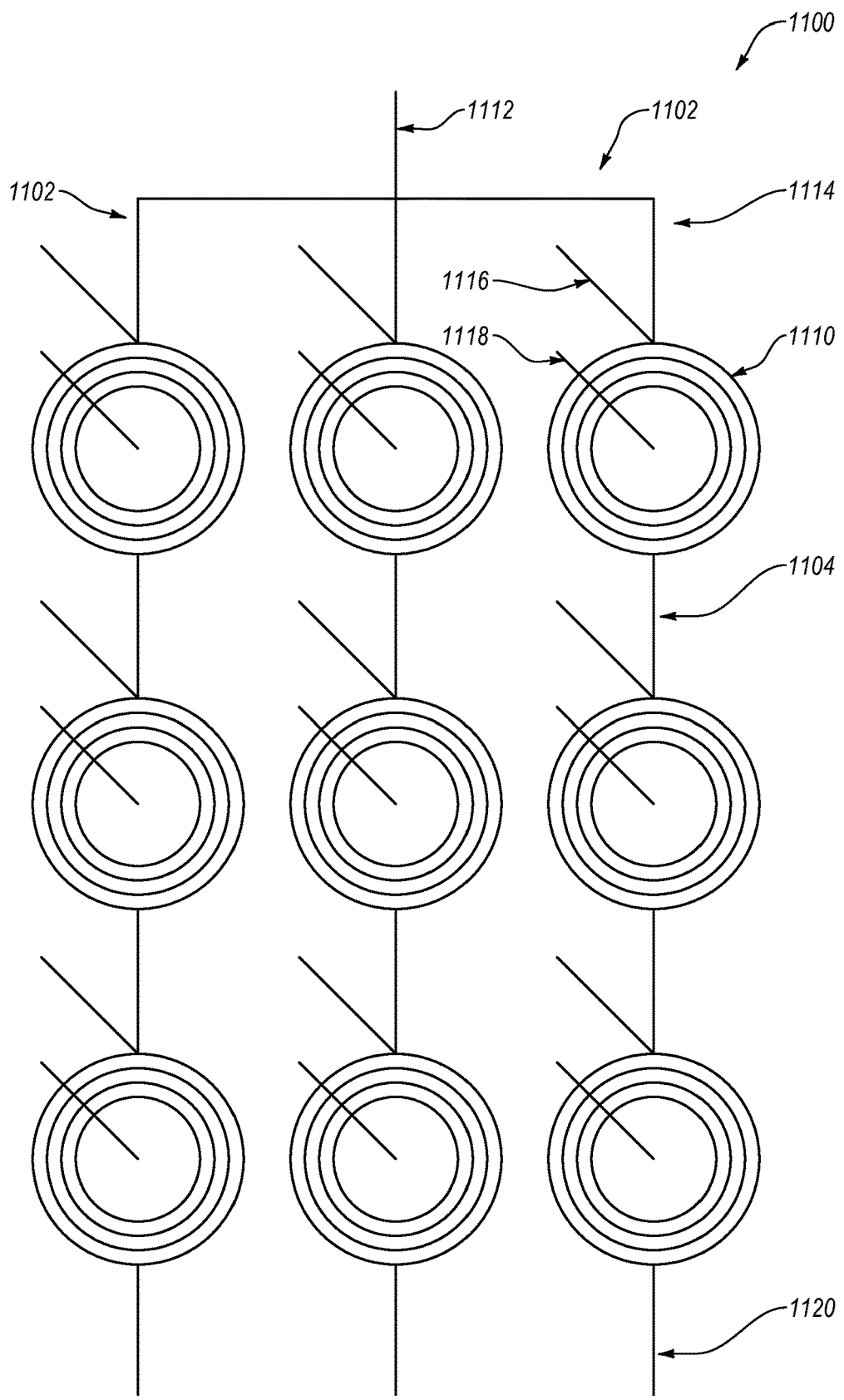
FIG. 11 illustrates an embodiment of a network showing parallel and/or series multi-chambered cell culture constructs.

FIG. 11 shows a network 1100 having multi-chamber constructs 1110 in parallel and series. Any of the connecting fluid pathways 1104 are optional. While a single inlet 1112 is shown for parallel analysis, each chain 1102 can include its own inlet 1114, and each multi-chamber construct 1110 can include its own inlet 1116 and central port 1118. The central port 1118 can be an inlet or outlet. The network 1110 can have individual outlets 1120 for each chain 1102; however, the outlets 1120 may be fluidly coupled into a single outlet in some instances. Any of the inlets 1116 or central ports 1118 can be optional. Also, the inlet 1112 and outlets 1120 may be inverted. This network may be IMN or SMN.

Figure 12:
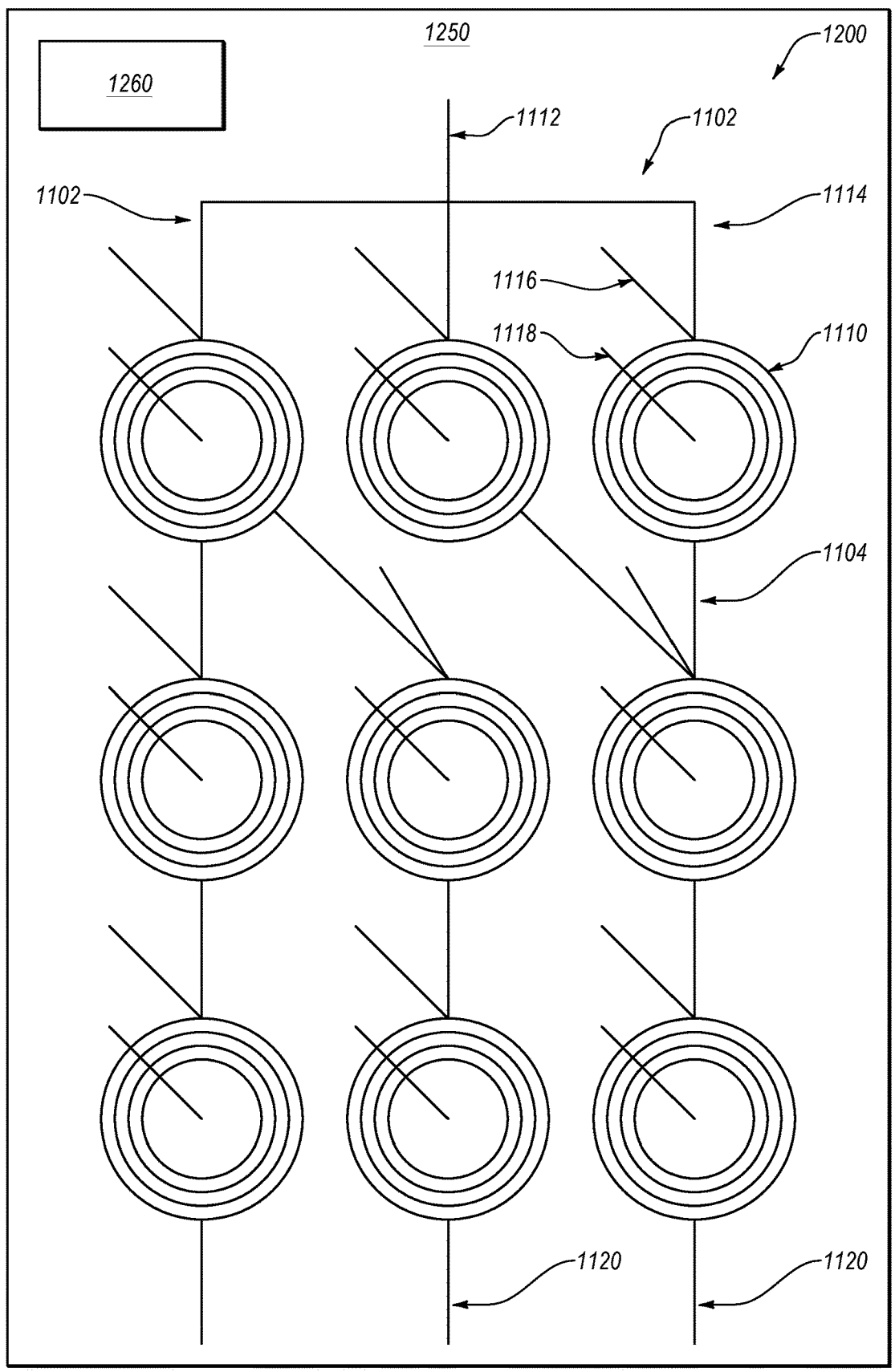
FIG. 12 illustrates an embodiment of parallel and series multi-chambered cell culture constructs having bifurcated outlets and joining inlets.

FIG. 12 includes a network 1200 having multi-chamber constructs 1110 in parallel and series. The connecting fluid pathways 1104 are shown so that the left chain includes a first multi-chamber construct 1110 with the outlet fluidly coupled with two multi-chambers constructs 1110 that are then each coupled to a single multi-chamber construct 1110. The right chain 1102 shows two first multi-chamber constructs 1110 with their outlets fluidly coupled with a single multi-chambers construct 1110 that is then coupled to a single multi-chamber construct 1110. This shows that any network arrangement of a plurality of multi-chamber constructs in parallel and/or series can be constructed, where inlets and outlets can be bifurcated, joined, branched, or other configuration in accordance with the description herein and in the incorporated references.

In one embodiment, the distinct chambers can have different cells or cell combinations for different cell cultures. The cell culture of each chamber can have a distinct function. For example, the outer chamber can have endothelial cells and simulate the outside of an organ, the barrier layer conduits can have cells that simulate the barrier layers of an organ, and the internal chamber can have cells that simulate the functionality of the organ.

The internal walls between the conduit chamber and organ tissue chamber can be porous so that fluid and/or nutrients can pass therebetween. In one option, the pores can be a dimension that is too small for cells to pass through; however, the pores can be enlarged in some embodiments so that cells may pass therethrough such as when modeling cancer cell migration or metastasis. In any event, various analytes, such as test analytes and metabolic analytes can pass through the pores of the porous walls. This can allow for a sequential encounter between an analyte or metabolites therefrom from the conduit chamber, through the barrier layer chambers, and then the organ tissue chamber. The dimension of the pores can vary. For example, the dimension of the pores can have a dimension up to 50 microns and as small as 100 nm; however, the dimension can range from about 200 nm to about 30 microns. The larger pores can be for cancer tissue modeling and allow for metastasis or cancer cells migrating between chambers. Generally, the pores can be smaller than 20 microns or smaller than 10 microns to control cell migration therethrough.

The pores can be symmetrical or asymmetric, ordered or random. The pore sizes can increase or decrease from one end (e.g., inlet) to other end (e.g., outlet) of pathway, or have size gradients therebetween, parabolic distributions therebetween, or any other distribution that provides a porous pathway between chambers. The pores on one side of the multi-chambered construct can be larger or smaller than the pores on the other side of the construct. The pores between the outer chamber and barrier chamber may be larger or smaller than the pores between the central chamber and barrier chamber. The pores between adjacent barrier chambers can be larger or smaller compared to the pores between the outer chamber and barrier chamber and/or central chamber and barrier chamber. In one example, the pores sizes decrease from the outer chamber to barrier chambers to central chambers. In another example, the pore sizes increase from the outer chamber to barrier chambers to central chambers.

The dimensions of the bottom wall, side walls, and/or top walls can range from about 5 microns to about 400 microns or up to about 500 microns, and possibly up to about 700 microns. The separation dimension between side walls can be about 5 microns, about 10 microns, about 25 microns, about 50 microns, about 100 microns, about 200 microns, about 250 microns, or about 400 microns, or any dimension therebetween. In one example, the height of the side walls can be about 5 microns to about 150 microns. The dimensions of the bottom and top walls of the chambers can be the same or different. For example, the chambers can be smaller from the outside in or from the inside out. The perforated walls can have a have a thickness that generally ranges from about 5 microns to about 500 microns, or such as for example 1 micron, 10 microns, 20 microns, 30 microns or up to 100 microns. In one example, the outside channel may be 100 microns wide, and then the barrier chambers may be maybe 200 microns wide. In one example, the barrier layers can be staggered with dimensions of 25 microns, 50 microns, 75 microns, and 100 microns. The number of barrier layer chambers can vary depending on the organ to simulate as well as the dimensions of the chambers. Each chamber can be large enough to culture enough cells to get some meaningful data during an assay, but the chambers should not be too large where diffusion times are too great and inhibit obtaining meaningful data.

The dimensions of the outer chamber and barrier chambers may be the same or different, which may include the dimension from one wall to another wall thereof. The thickness of the walls between the outer chamber and barrier chambers or between the different barrier chambers or between the barrier chambers and central chamber may be the same or different. These dimensions can increase from the outside to the central chamber or they may decrease from the outside to the central chamber, such as in an increasing or decreasing size gradient for the chambers and/or walls. The dimensions may also be parabolic with increasing to decreasing to increasing, or from decreasing to increasing to decreasing relative dimensions of the chamber and/or walls.

Virtual experiments using Computational Fluid Dynamics (CFD) or other computational modeling allow the ability to optimize the experimental protocols. This procedure not only saves time but also reduces reagent consumption. CFD modeling can also be used to differentiate between perfusion based vs. diffusion based experiments in addition to determining the flow rate ranges for optimal cell growth. CFD modeling can also drive design optimization of each of the conduits and layers of the device ranging from distance for diffusion, pore size, number of pores.

The porous walls can be configured to provide a diffusion barrier between adjacent chambers. This can provide a diffusion barrier between the vascular space (e.g., outer conduit chamber) and tissue space (e.g., internal organ tissue chamber).

The different chambers can be arranged in a side-by-side format as illustrated, but other configurations, such as stacked, sandwiched, volumetric, or concentric can be employed. In one embodiment, the different chambers can be arranged similar to the layers of an onion. Generally, the outer chamber is used for introducing test analytes; however, the inner chamber can be used for introducing test analytes. In some options, the boundary layer chambers can be used for introducing test analytes as each boundary conduit can have unique inlets and/or outlets. Alternatively, all of the boundary conduits can have a common inlet and a common outlet. When an internal conduit is included, it can be used for introducing test analytes directly to the organ tissue chamber for an organ tissue simulation. Thus, generally the inner most conduit or outermost conduit can serve to provide the test analytes, which test analytes or metabolites thereof can pass through the boundary layers by passing through the pores. Also, the conduits can be configured to selectively provide different nutrients to the different types of cell cultures, where the outer conduit (endothelial cells) and internal organ tissue chamber (tissue cells) receive different nutrients compared to one or more boundary layers. Each boundary layer may receive different nutrients, or they can all receive the same nutrients.

The internal chamber is shown to have an inlet fluid pathway that opens into a space that is larger than the inlet fluid pathway. The internal chamber can be wider with a larger cross-sectional profile than the inlet and outlet fluid pathways. The porous internal walls that define the internal chamber can diverge from each other from the inlet toward the outlet until a medial point at which the porous internal walls converge toward each other until reaching the outlet. The divergence and convergence can result in a spherical, oval, oblong, or polygon shape, such as a hexagon. The porous walls defining the boundary layers and outer conduit layer can have the same shaping as the porous internal walls, and may have the same divergence and convergence between the inlets and outlets. In one embodiment, the entirety of the walls between the internal chamber and outer non-porous perimeter wall can be porous walls that are porous from the inlets to the outlets. The cross-sectional profile or distance between the porous internal walls can be from about 1.5 to 50 times larger than the boundary layer chambers cross-sectional profiles or distance between the porous walls that define the boundary layer chambers. The cross-sectional profile or distance between the porous internal walls can be from about 1.5 to 50 times larger than the outer chamber cross-sectional profiles or distance between the porous walls that define the outer chambers.

In one embodiment, the outer chambers and boundary chambers can be partitioned into right and left sides as shown in FIG. 1A. In one option, the internal chamber can be partitioned into right and left sides as shown in FIG. 5 when an internal conduit is included. The right and left chamber sides can be considered together to be a complete chamber. The right and left chamber sides can be fluidly coupled such as by having a common inlet and a common outlet or a flow path that fluidly couples the right and left sides. However, the right and left chamber sides may be separate chambers with separate inlets and separate outlets from each other. The right and left chambers sides can be used for the same studies or test analytes, or different test analytes can be introduced into the right and left chambers.

The cells can grow only on the bottom, or can grow to confluence on the sides and optionally the top walls. As such, the cells can grow over the pores. Preferably, the cells grow completely around the chambers to form a cellular lumen or three-dimensional tissues. Tissue culture scaffold materials can be located in any or all of the chambers as desired. The cells can grow over the pores but allow analytes or metabolites or other fluid to pass through the pores to an adjacent chamber. So, the cells start growing at the bottom first, but eventually they fill up the porous side walls and the top walls and all around the chambers.

In a preferred embodiment, the distinct chambers can be side-by-side or horizontally sandwiched. The device can include the chambers being the same height so that the height is maintained across each chamber. Also, the device can be prepared so that the chambers are parallel to each from the outside chamber to the internal chamber. The device can include an outside conduit or outside chamber on the outside of the device that functions as a conduit, where the chamber has a bottom surface and two sidewalls—one is an outside perimeter side wall and one is an inside perimeter side wall that has perforations or is otherwise porous. Each of the other chambers can be similarly configured with all internal walls being porous. A top wall can enclose all of the chambers as shown.

Each chamber can provide a tissue space that includes tissue culture scaffolds that will help grow the cells in a 2D monolayer or in a 3D sense to substantially filling up the entire space of the chamber. In the absence of the scaffolds, the cells will just cover the walls (e.g., bottom, side and/or top). Whereas the tissue scaffolds provide a 3D cell culture in a nice, packed structure in the tissue space. The scaffolds can be the same or different material from the walls. The scaffolds can be integrated or coupled with the walls, or inserted into the chambers. The scaffolds can be cast in the same method when the walls of the chambers are cast.

The multi-chambered cell culture device can be manufactured in accordance with known principles, such as in the incorporated references. The devices can be made by providing a master and then pouring a polymer over it, then bake or otherwise curing the polymer so the polymer hardens, and then peeling the polymer from the master (e.g., mold). There can be a negative of the device on the master, which provides the device when cast with the polymer. The device can then be attached to a top wall, such as polymer or glass. The stamp or mold can be prepared to define all the features of the device. Also, the chambers can include collagen or matrigel or other gelatinous cell culture scaffold material. In addition, natural or synthetic culture scaffolds can be used. Also, electrospun fibers (comprising of culture matrix, proteins and other biological and artificial components) can be used for the scaffolds. Cells can be mixed with scaffolds on cultured on scaffolds for creating a 2D or 3D culture.

In one embodiment, a plate can include a plurality of multi-chambered cell culture wells. That is, a well plate can include a plurality of wells configured with the multiple chambers as described herein. The wells can be engineered with appropriate inlets and outlets as described herein. The plate may include the inlets and outlets between the wells. For example, a well plate of a standard size that fits in a plate reader having 96 wells can be configured to include a multi-chambered cell culture well in one or more wells or in each of the 96 wells. Well plates with smaller numbers of multi-chambered wells may also be prepared. The multi-chambered cell culture wells can be configured the same or different. For example, a single well plate can be configured with two or more different organ models, which may be separate, or linked in a biologically relevant series. The multi-chambered device can be configured as a well, or configured as an insert that is dropped into a well.

The cross-sectional profile of the multi-chambered cell culture device and individual chambers, such as the internal chamber, can have any shape, such as circular, triangle, square, rectangle, pentagon, hexagon, or other polygon as well as irregular.

The distinct chambers can have distinct cell cultures. The cells can be any type of cell ranging from immortalized cell lines to primary cells to patient-derived cells. In some instances, a tissue culture from a patient can be included in a distinct chamber. The cell cultures can include a single type of cell or a combination of cells, such as 2, 3, or 4 different types in a co-culture. In some natural tissues, multiple cells may be present, and such tissues can be simulated with a similar cell type combination.

The multi-chamber cell culture device may be connected to a flow or pressure regulating system that can regulate the pressure across the distinct chambers or within each distinct chamber. Pumps and valves can be used to regulate the pressure. As such, operation of the device can include regulating the pressures inside each of the chambers such as the outer conduit. For example, a tissue such as liver or the kidney may be leaky, pressure control can be used to simulate such leakiness of the tissue. Also, some tissue like the brain and tumor can have very high pressures, which can be simulated with controlling the pumps and valves. The system can regulate the pressure in each of these distinct chambers as desired to mimic normal vs. diseased conditions.

The pressure can be selectively controlled by valves under the operation of a control system. The control system can include a memory device having computer executable instructions for selectively controlling valves of the device in order to regulate pressure. The valves can be prepared from the same or different materials as the body of the device, or they can be separate materials that are inserted into ports in the device at discrete locations. Each discrete chamber can have one or more valves for pressure regulation, which may be located in the top wall. Two valves can be used as an inlet and an outlet, as illustrated. The device may include a fluid pathway inlet and outlet with valves as well as a pressure inlet valve and pressure outlet valve in the top wall. Fluid pathway valves can regulate fluid flow, while the pressure valves can regulate pressure within the chambers.

The multi-chambered cell culture device can be used for any purpose involving cell culture. The multi-chambered cell culture device can be used in cell culture methods to simulate an organ. The methods can include testing one or more analytes for a presence or absence of biological response from the simulated organ. The biological response can be from the one or more analytes modulating a biological pathway, cell function, metabolic function, or toxicity. Any of the studies described herein or in the incorporated references can be performed with the multi-chambered cell culture device. The one or more analytes can be provided to the simulated organ in any possible manner, such as by being introduced into the outer chamber, one or more barrier layer chambers, or internal chamber.

The device can be used to test the effect of any substance on the cells or simulated organ, and vice versa. The substance can be a biologically active agent that can be any agent that is administered for a function, such as a biological function to improve or otherwise modulate a biological process, such as a biological pathway. However, the agent can be active, such as to emit light, without being biologically active. As such, the biologically active agent can be a traditional pharmaceutical or nutraceutical, and it can be any type of substance for testing or diagnostics. The biologically active agent can be any agent that is administered to a subject in order to elicit a biological response that arises from the biological activity of the agent. The biological response obtained can be a measurable biological response or provide some change that can be analyzed and determined, such as by testing to determine an amount of the biologically active agent to be administered. The biologically active agent can be a toxin or poison or other deleterious substance. Examples can include the biologically active agent being a mineral, vitamin, pharmaceutical, nutraceutical, small molecule, macromolecule, organic molecule, polypeptide, protein, nucleic acid, polynucleotide, derivatives thereof, and combinations thereof. The biologically active agent can be for a human or animal subject. Human and veterinary medicines can be evaluated and improved with the present invention. The substance can be an agricultural agent such as herbicides, pesticides, and/or fertilizers. The substance can be an environmental substance that is natural or manmade and found in the environment. The substance can be a particle. The substance can be a foreign cell not found in an organ, such as a cancer cell, bacteria, yeast, or the like, and even a virus. The test substance can be a particle, such as a nanoparticle, liposome, microparticle, or microsphere or any other similar type of particle.

The test substance can even be a substance commonly used in a pharmaceutical product or combination thereof to test for activity in certain simulated organs. The test substance can include the following: a film-forming agent; a filler; a plasticizer; a taste-masking agent; a coloring agent; a solubilizing agent; an effervescent agent; an antioxidant; an absorption enhancer; a disintegrating agent; a pH modifying or buffer agent; a surfactant; a complexing agent; a bioadhesive agent; a sheet adhesive; an identifying agent; an anti-counterfeiting agent; a tracking agent; transporter inhibitor agent; transporter inducer agent; emulsifying agent, self-emulsifying system agents; crystallization inhibitor; crystallization promoter; supersaturation promoting agent; antimicrobial preservative; catalyst; chelating agent; particles; organoleptic agent; flavoring agent; scent agent; identifying device; and/or anti-counterfeiting device.

In one embodiment, cells can be analyzed in any of the chambers. However, in some assays, only the cells in the internal chamber will be assayed. For example, visual analysis, such as with a microscope can be used for analysis of the cells. In another example, the cells can be identified using optical or electrical methods. For example, cell staining markers specific for cell types can be used. In addition, electrical signals based detection can allow detection of morphology changes (cell differentiation) and different types of cells.

In one embodiment, a cell culture device can include: a top wall; a bottom wall; one or more perimeter walls coupled with and extending between the top wall and bottom wall; and at least 3 distinct chambers between the top wall, bottom wall. The one or more perimeter walls can include: an internal chamber defined by at least one porous internal wall and having an internal chamber inlet and an internal chamber outlet; one or more boundary layer chambers having at least an inner boundary layer chamber defined by the at least one porous internal wall and at least one porous inner boundary layer wall, the at least one porous internal wall having a plurality of pores fluidically coupling the central internal chamber to the one or more boundary layer chamber; and an outer chamber defined by an outer porous boundary layer wall of the at least one porous boundary layer walls and the one or more perimeter walls and having an outer conduit chamber inlet and an outer conduit chamber outlet, the outer porous boundary layer wall having a plurality of pores that fluidically couple the outer conduit chamber with the one or more boundary layer chambers. In one aspect, wherein the at least three distinct chambers are nonlinear and/or idealized. In one aspect, the internal chamber is central to and surrounded by the one or more boundary layers. In one aspect, the internal chamber is concentric with the one or more boundary layers. In one aspect, the internal chamber is central to and surrounded by the one or more boundary layers and outer conduit chamber. In one aspect, the internal chamber is concentric with the one or more boundary layers and outer conduit chamber.

In one embodiment, the at least one porous internal wall includes pores distributed from a first and to an opposite second end. The pores can be holes in the walls or gaps between posts or wall portions. In one aspect, the at least one porous boundary layer wall includes pores distributed from a first and to an opposite second end. In one aspect, all walls between the top wall, bottom wall, and one or more perimeter walls are completely porous.

In one embodiment, the internal chamber inlet and outlet are at formed by internal chamber inlet walls and internal chamber outlet walls extending between the top wall and bottom wall. In one aspect, the outer conduit chamber inlet and outlet are at formed by outer conduit chamber inlet walls and outer conduit chamber outlet walls extending between the top wall and bottom wall. In one aspect, one or more of the boundary layer chambers include a boundary layer chamber inlet and a boundary layer chamber outlet. In one aspect, the boundary layer chamber inlet and boundary layer chamber outlet are at formed by internal chamber inlet walls and internal chamber outlet walls extending between the top wall and bottom wall.

In one embodiment, one or more of the inlets and/or one of more of the outlets are ports formed into one of the walls. In one aspect, the ports are formed into the top wall. In one aspect, one or more of the ports include a valve. In one aspect, one or more of the inlets and/or one or more of the outlets include valves. In one aspect, one or more of the boundary layer chambers includes an inlet port having an inlet valve and/or an outlet port having an outlet valve.

In one embodiment, the internal chamber includes a first porous internal wall and opposite second porous internal wall with the internal chamber therebetween, and both the first porous internal wall and second porous internal wall extending between the internal chamber inlet and outlet.

In one embodiment, the boundary layer chamber includes a first boundary layer wall and opposite second porous boundary layer wall with the internal chamber and boundary layer chamber therebetween. In one aspect, the boundary layer chamber encompasses the internal chamber. In one aspect, both the first porous boundary layer wall and second porous boundary layer wall extending between a boundary layer inlet and boundary layer outlet.

In one embodiment, at least one of the outer chamber, boundary layer chamber, or internal chamber, or inlet or outlet thereof, is configured as an idealized microvascular network (IMN).

In one embodiment, at least one of the outer chamber, boundary layer chamber, or internal chamber, or inlet or outlet thereof is configured as a synthetic microvascular network (SMN).

In one embodiment, the pores of the porous walls have a cross-sectional dimension ranging from 5 nm to 500 microns. This can be the size of the posts. In one aspect, the porous walls have a width and/or height and/or thickness ranging between 5 microns and 500 microns.

In one embodiment, one or more of the outer chamber, boundary layer chamber, or internal chamber has a width ranging between 5 microns and 500 microns.

In one embodiment, the bottom and side walls are integrated and the top wall is coupled to top ends of the side walls. In one aspect, the side walls, boundary layer walls, outer conduit walls, internal walls extend from and are integrated with the bottom wall.

In one embodiment, each wall separating adjacent chambers is porous. In one aspect, the porous walls have pores located from the top wall to the bottom wall. In one aspect, the pores are contained within a wall. In one aspect, the pores are gaps between adjacent wall segments.

In one embodiment, the cell culture device if operably coupled to a pump system. In one aspect, the side walls, boundary layer walls, outer conduit walls, internal walls extend from and are integrated with the bottom wall. In one aspect, the inlets and/or outlets are operably coupled to a pump system and analyte reservoir. In one aspect, valves in ports of the top surface are coupled to a chamber pressure regulating pump system.

In one embodiment, the device can include: a first cell culture in the outer chamber; a second cell culture in one or more of the boundary layer conduits that is a different type from the first cell culture; and a third cell culture in the internal chamber that is a different type from at least one of the first cell culture and second cell culture. In one aspect, the first, second, and third cell cultures are all different types. In one aspect, the cell cultures include cells larger than the pores. In one aspect, the porous walls separating the one or more chambers include cells growing over the pores. In one aspect, the first cell culture includes endothelial cells. In one aspect, the second cell culture include cells found in organ boundary layers. In one aspect, the second cell culture include cells found in organ boundary layers selected from brain, liver, heart, kidney, lung, stomach, intestines, pancreas, ovary, cervix, spleen, arteries, venules, capillaries and stem cells. In one aspect, the third cell culture include cells found in organ tissue layers. In one aspect, the second cell culture include cells found in organ tissue boundary layers selected from epithelial, connective, muscle, bone and nervous tissue in addition to cells representing the germ layers originating from stem cells. In one aspect, the combination of the first, second, and third cell cultures simulates an organ from an endothelial surface, through organ boundary layers, and internal cells.

In one embodiment, an automated cell culture system 1250 (See FIG. 12) can include: the cell culture device having one or more multi-chambered constructs as described herein; and a computing system 1260 (see FIG. 12) operably coupled to the cell culture device and having a memory device with computer executable instructions for controlling fluid flow of the chambers independently. The computing system 1260 can be configured to control any valve in any chamber for automated cell culture methods for various assays. The computing system 1260 and automated cell culture system 1250 can be utilized with any of the embodiments of the invention described herein.

In one embodiment, a cell culture device can include: a top wall; a bottom wall; one or more perimeter walls coupled with and extending between the top wall and bottom wall; and at least five distinct chambers between the top wall, bottom wall. The one or more perimeter walls comprising: an internal chamber defined by at least one porous internal wall and having an internal chamber inlet and an internal chamber outlet; three or more boundary layer chambers having at least an inner boundary layer chamber defined by the at least one porous internal wall and at least one porous inner boundary layer wall, the at least one porous internal wall having a plurality of pores fluidically coupling the central internal chamber to the one or more boundary layer chamber; and an outer chamber defined by an outer porous boundary layer wall of the at least one porous boundary layer walls and the one or more perimeter walls and having an outer conduit chamber inlet and an outer conduit chamber outlet, the outer porous boundary layer wall having a plurality of pores that fluidically couple the outer conduit chamber with the one or more boundary layer chambers. In one aspect, the at least five distinct chambers are nonlinear SMN or idealized IMN configurations.

In one embodiment, one or more conduits include a substance. In one aspect, one or more conduits include a gel.

In one aspect, one or more conduits include collagen. In one aspect, one or more conduits include laminin. In one aspect, one or more conduits include matrigel. In one aspect, one or more conduits are devoid of cells. In one aspect, one or more conduits include a natural or synthetic biological matrix capable of cell culture. In one aspect, one or more conduits include a biological matrix configured for growing cells. In one aspect, one or more conduits include a biological matrix and cells. In one aspect, some of the pores are filled with a gel. In one aspect, all of the pores in a wall separating chambers are filled with a gel. In one aspect, some or all of the pores in a wall separating chambers are filled with matrigel. In one aspect, all of the pores in a wall separating chambers are smaller than a cell. In one aspect, all of the pores in a wall separating chambers are larger than a cell.

In one embodiment, the device can include one or more idealized microvascular networks connected to one or more of the inlets or outlets of one of the chambers.

In one embodiment, the device can include one or more synthetic microvascular networks connected to one or more of the inlets or outlets of one of the chambers.

In one embodiment, a cell culture device can include: an onion-like chamber system having three or more of distinct chambers between a top wall, bottom wall, and one or more perimeter walls. The onion chamber system can include: an internal chamber defined by at least one porous internal wall and having an internal chamber inlet and an internal chamber outlet; three or more boundary layer chambers having at least an inner boundary layer chamber defined by the at least one porous internal wall and at least one porous inner boundary layer wall, the at least one porous internal wall having a plurality of pores fluidically coupling the central internal chamber to the one or more boundary layer chamber; and an outer chamber defined by an outer porous boundary layer wall of the at least one porous boundary layer walls and the one or more perimeter walls and having an outer conduit chamber inlet and an outer conduit chamber outlet, the outer porous boundary layer wall having a plurality of pores that fluidically couple the outer conduit chamber with the one or more boundary layer chambers. In one aspect, wherein the onion chamber is nonlinear or idealized. In one aspect, the device can include plurality of onion chamber systems coupled together. In one aspect, the device can include a plurality of onion chamber systems separate from each other. In one aspect, the cells in conduits or chambers of the device can be identified using optical and/or electrical based detection.

In one embodiment, the multi-chambered constructs can be used in a cell culture assay, which can include incubating calls in one or more of the chambers and testing an interaction of a substance with the cells of one or more of the chambers. The substance can be any substance, and can be molecule, protein, nucleic acid, cell, bacteria, virus, or other.

In one embodiment, a method of testing an analyte can include obtaining the cell culture device having one or more multi-chambered constructs; introducing a test analyte into one of the outer chamber, boundary layer chamber, or internal chamber; incubating the test analyte with one of the first, second or third tissue cultures; and determining whether or not the test analyte had an effect on the first, second, or third tissue cultures. In one aspect, the method can include simulating a pressure profile across the outer chamber, boundary layer chamber, or internal chamber with the valves. In one aspect, the method can include facilitating passage of the analyte into an adjacent chamber. In one aspect, the method can include facilitating passage of the analyte into through an adjacent chamber and into a third chamber. In one aspect, the method can include facilitating passage of a metabolite of the analyte into an adjacent chamber. In one aspect, the method can include facilitating passage of a metabolite of the analyte into an adjacent chamber into a third chamber. In one aspect, the method can include determining a change in one or more of the first, second, or third cell culture in response to the test analyte.

In one embodiment, and assay method can include: performing an assay to measure a parameter for one or more of the first, second, or third cell culture; and determining a difference in the parameter between one of the first, second, or third cell culture compared to another.

In one embodiment, an assay method can include: introducing a test reagent that interacts with the test analyte or metabolite thereof into one of the first, second, or third cell culture; and detecting an interaction between the test reagent and test analyte in one of the first, second, or third cell culture. In one aspect, the method can include tracking the test analyte passage between two of the outer chamber, boundary layer chamber, and internal chamber.

In one embodiment, an assay method can include introducing the test analyte into the outer chamber; and determining an effect of the test analyte or metabolite thereof on the third cell culture.

In one embodiment, an assay method can include simulating with the device an organ of a body.

In one embodiment, an assay method can include determining a diffusion parameter of the test analyte from the outer chamber, through the boundary layer chambers, and into the internal chamber.

In one embodiment, an assay method can include using optical and/or electrical based detection to identify the cells in conduits or chambers of the device.

The present invention provides apparatus and methods that can be used to study fluid flow and particle adhesion in physiological vessels including arterioles, capillaries, venules, and microvascular networks comprising any combination of the three. The same apparatus and methods can also be used to optimize drug delivery in the microvasculature. Many drugs are available in microencapsulated, liposomal/lipisomal, and other micro and nanoscale particle forms. The adherence and uptake of these particles in the microvasculature depends on specific and non-specific interactions between the surfaces of drug delivery particles and endothelial cells that line the walls of the microvasculature. Adhesion also depends on fluid dynamics parameters such as flow velocities and shear forces which, in turn, depend on vascular network geometries. The present invention provides microfluidic chips comprising synthetic microvascular networks (SMNs) with flow channels that possess key geometric and topological features that cause them to display the same types of fluid flow patterns and particle adhesion patterns as are found in physiological microvascular networks. In addition, the SMNs require quantities of reagents that are reduced by orders of magnitude compared with currently used techniques. Known microfabrication techniques also allow for development of plastic, disposable chips eliminating concerns of cross-contamination.

A "synthetic microvascular network" (SMN) is a man-made network that comprises a plurality of interconnected flow channels that form geometrical features and have fluid flow properties found in physiological microvascular networks. The flow channels (synthetic vessels) form intersecting networks and may be arranged end to end, analogous to an arteriole, capillary, venule sequence. Flow channels and the SMNs they form possess one or more geometric characteristics of physiological microvascular selected from variable cross-sectional shapes, variable cross-sectional areas, convolutions, turns, and anastomoses. A network consisting entirely of linear channels with constant cross sectional areas, for example, is not a SMN because such a network does not possess the required physiological characteristics of a physiological microvascular network. One or more flow channels of a SMN may comprise walls made of a porous material such that fluid may move from the interior (lumen) of the flow channel into a space (e.g., multi-chamber construct) external to the lumen in a manner similar to the movement of fluid from the lumen of a physiological vessel into an interstitial space, or vice versa.

An Idealized microvascular network (IMN) is a man-made network comprising interconnected flow channels that have certain fluid flow properties found in physiological microvascular networks. The diameters of the channels range from 10-500 microns and comprise of angles typically between 15 degrees and 135 degrees.

Flow channels in a multi-chambered construct based on IMNs comprise porous walls (0.2-5 microns) such that liquid may move between chamber, such as a manner similar to the movement of fluid from the lumen of a physiological vessel into an interstitial space or vice versa. As used herein, the term "idealized" in association with a microfluidic network, junction, or bifurcation is used to describe a synthetic network, junction, or bifurcation consisting of straight microfluidic channels joined at acute, right, or obtuse angles.

As used herein, a microfluidic channel may have a rectangular, circular, semi-circular, irregular or a combination of cross-sectional shapes. The dimensions of a channel are described, for example, by length, depth and width wherein the depth is measured perpendicular to the plane of a microfluidic chip containing the channel and length and width are measured in directions lying in the plane of the microfluidic chip containing the channel. Channels having circular or semi-circular cross-sections may be described as having variable depth and width relative to channels having rectangular cross-sections or may alternatively be described in terms of channel diameter. Maximum depth and width when used to describe a channel having a circular or semi-circular cross-section are both equal to the maximum diameter of the channel. When used to describe a channel having a rectangular cross-section, the maximum width and depth refer to the constant width and depth of a channel having a constant width and depth or to the highest values for width and depth for channels having variable width and depth.

In a non-limiting example, a microfluidic chip having one or more multi-chamber constructs is constructed using techniques employed in the semiconductor industry such as photolithography, wet chemical etching, thin film deposition and soft lithography using polymeric substrates, such as Polydimethylsiloxane (PDMS). Other materials that may be used in place of PDMS include Poly(Styrene Butadiene Styrene) (SBS) and Poly(Styrene-Ethylene-Butadiene-Styrene) (SEBS) elastomers, Polyester-ether (PEE) thermoplast, and thermoset polyester (TPE), which can be used for replica molding fabrication techniques. Polyolefin plastomer (POP's) can be specifically used for submicron range channels. Glass or quartz with reactive wet/dry etching of the microchannels can also be used. Thermoplastic materials such as polymethylmethacrylate (PMMA), polycarbonate (PC), cyclic olefin copolymer (COC), polystyrene (PS), poly vinyl chloride (PVC), and polyethylene terephthalate glycol (PETG) can be used with embossing techniques or injection molding. PS, PC, cellulose acetate, polyethylene terephthalate (PET), PMMA, PETG, PVC, PC, and polyimide can also be used with laser ablation techniques. In general, a microfluidic chip is formed with a number of microchannels that are connected to a variety of reservoirs containing fluid materials. The fluid materials are driven or displaced within these microchannels throughout the chip using electrokinetic forces, pumps and/or other driving mechanisms. Other manufacturing techniques can be used.

In one embodiment, the outer chamber can be devoid of an inlet and/or outlet. In one embodiment, the one or more boundary layer chambers can be devoid of an inlet and/or outlet. In one embodiment, the internal chamber can be devoid of an inlet and/or outlet. With the proviso that the multi-chamber cell culture device includes at least one inlet, and preferably also includes at least one outlet.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety, including: U.S. Pat. Nos. 7,725,267; 8,175,814; U.S. 20100099136; U.S. 2009/0023608; U.S. 2009/0203126; U.S. 20100112550; U.S. Ser. No. 13/332,400; U.S. 20100227312; and U.S. 20110104658. The multi-chambered device can be designed, manufactured, and used in accordance with the principles and for the study of diseases or disease states of the incorporated references.

The invention claimed is:
1. A method of testing an analyte, the method comprising:
obtaining a cell culture device, the cell culture device comprising:
  a top wall;
  a bottom wall;
  one or more perimeter walls coupled with and extending between the top wall and bottom wall; and
  a plurality of distinct chambers between the top wall, bottom wall, and one or more perimeter walls comprising:
    an internal chamber defined by at least one porous internal wall and having an internal chamber inlet and an internal chamber outlet and having a first cell culture;
    one or more boundary layer chambers having at least an inner boundary layer chamber defined by the at least one porous internal wall and at least one porous inner boundary layer wall, the at least one porous internal wall having a plurality of pores fluidically coupling the central internal chamber to the one or more boundary layer chamber and having a second cell culture; and
    an outer chamber defined by an outer porous boundary layer wall of the at least one porous boundary layer walls and the one or more perimeter walls and having an outer chamber inlet and an outer chamber outlet, the outer porous boundary layer wall having a plurality of pores that fluidically couple the outer chamber with the one or more boundary layer chambers and having a third cell culture,
wherein each of the plurality of distinct chambers is nonlinear or idealized;
introducing a test analyte into one of the outer chamber, boundary layer chamber, or internal chamber;

incubating the test analyte with one of the first cell culture, second cell culture, or third cell culture; and determining whether or not the test analyte had an effect on the first cell culture, second cell culture, or third cell culture.

2. The method of claim 1, comprising flowing a fluid:

through the internal chamber from the internal chamber inlet to the internal chamber outlet;

through the one or more boundary layer chambers; and/or through the outer chamber.

3. The method of claim 2, wherein:

each of the one or more boundary layer chambers has a boundary layer inlet and a boundary layer outlet with the fluid flowing therebetween; and/or the outer chamber has an outer chamber inlet and an outer chamber outlet with the fluid flowing therebetween.

4. The method of claim 3, wherein at least one pump is operably coupled with:

the internal chamber inlet;

each boundary layer inlet; and/or the outer chamber inlet.

5. The method of claim 4, comprising controlling an inlet valve and/or outlet valve so as to control the fluid flow in:

the internal chamber;

each boundary layer; and/or the outer chamber.

6. The method of claim 3, wherein at least one fluid reservoir is operably coupled with:

the internal chamber inlet;

each boundary layer inlet; and/or the outer chamber inlet.

7. The method of claim 1, comprising:

simulating a pressure profile across the outer chamber, boundary layer chamber, and/or internal chamber.

8. The method of claim 2, comprising:

facilitating passage of the analyte into an adjacent chamber.

9. The method of claim 2, comprising:

facilitating passage of the analyte into through an adjacent chamber and into a third chamber.

10. The method of claim 2, comprising:

facilitating passage of a metabolite of the analyte into an adjacent chamber.

11. The method of claim 2, comprising:

facilitating passage of a metabolite of the analyte into an adjacent chamber into a third chamber.

12. The method of claim 2, comprising:

determining a change in one or more of the first cell culture in the internal chamber, the second cell culture in the one or more boundary layer chambers, and/or the third cell culture in the outer chamber in response to the test analyte.

13. The method of claim 1, comprising:

performing an assay to measure a parameter for one or more of the first cell culture, second cell culture, or third cell culture; and determining a difference in the parameter between one of the first cell culture, second cell culture, or third cell culture compared to another.

14. The method of claim 1, comprising:

introducing a test reagent that interacts with the test analyte or metabolite thereof into one of the first cell culture, second cell culture, and/or third cell culture; and detecting an interaction between the test reagent and test analyte in one of the first cell culture, second cell culture, or third cell culture.

15. The method of one of claim 1, comprising:

tracking the test analyte passage between two of the outer chamber, one or more boundary layer chambers, and internal chamber.

16. The method of claim 1, comprising:

introducing the test analyte into the outer chamber; and determining an effect of the test analyte or metabolite thereof on the first cell culture.

17. The method of claim 1, comprising simulating with the device an organ of a body with perfusion.

18. The method of claim 1, comprising:

determining a diffusion parameter of the test analyte from the outer chamber, through the boundary layer chambers, and into the internal chamber.

19. The method of claim 1, comprising using optical and/or electrical based detection to identify the cells of the device.

20. The method of claim 2, comprising controlling the fluid flow with a controller.

21. The method of claim 1, wherein the test analyte is selected from the group consisting of a mineral; a vitamin; a pharmaceutical agent; a nutraceutical agent; small molecule; macromolecule; organic molecule; polypeptide; protein; nucleic acid; polynucleotide; nanoparticle; liposome; microparticle; microsphere; toxin; poison; a film-forming agent; a filler; a plasticizer; a taste-masking agent; a coloring agent; a solubilizing agent; an effervescent agent; an antioxidant; an absorption enhancer; a disintegrating agent; a pH modifying or buffer agent; a surfactant; a complexing agent; a bioadhesive agent; a sheet adhesive; an identifying agent; an anti-counterfeiting agent; a tracking agent; transporter inhibitor agent; transporter inducer agent; emulsifying agent, self-emulsifying system agents; crystallization inhibitor; crystallization promoter; supersaturation promoting agent; antimicrobial preservative; catalyst; chelating agent; particles; organoleptic agent; flavoring agent; scent agent; identifying device; anti-counterfeiting device, or combinations thereof.

* * * * *